United States Patent [19]

Christophers et al.

[11] Patent Number: 5,234,911
[45] Date of Patent: Aug. 10, 1993

[54] SUBSTANCE WITH INTERLEUKIN-8 INHIBITING ACTIVITY AND PROCESS FOR ITS PREPARATION

[75] Inventors: Enno Christophers, Kiel; Jens-Michael Schröder, Blumenthal, both of Fed. Rep. of Germany

[73] Assignee: Gist-brocades, N.V., Delft, Netherlands

[21] Appl. No.: 642,119

[22] Filed: Jan. 16, 1991

[30] Foreign Application Priority Data

Jul. 9, 1990 [EP]  European Pat. Off. ........ 90201841.5

[51] Int. Cl.$^5$ ...................... A61K 37/02; C07K 3/02; C07K 15/06
[52] U.S. Cl. ........................................ 514/21; 514/12; 530/350; 530/351; 530/412; 530/842
[58] Field of Search ............... 530/414, 412, 350, 351, 530/842; 514/12, 21; 424/85.2

[56] References Cited

U.S. PATENT DOCUMENTS 5,079,228  1/1992  Cohen et al. ............................ 514/3

OTHER PUBLICATIONS

Siegbahn et al. Scand. J. Haematol., vol. 35, No. 1, pp. 80–87 (1985).
Lewin, Science, vol. 237, Sep. 25 (1987).
Mrowietz et al., XIX Meeting of ADF, p. 85 Nov. 1991 Abstract.
Köck et al, Pharmacol. Skin. Basel, vol. 4, pp. 6, 1–7. (1991).
Swensson et al., J. Invest. Dermatol., vol. 96, No. 5, pp. 682–689 (1991).
Leonard et al., J. Invest. Dermatol., vol. 96, No. 5, pp. 690–694 (1991).
Siegbahn et al., Scand. J. Haematol., vol. 35(1), pp. 80–87 (1985) (Abstract).
Miller et al., FASEB (Fed. Am. Soc. Exp. Biol.) J4 (7), 1990, A2117.
Donabedian et al., Infect. Immun., vol. 40 (3), pp. 1030–1037 (1983).
Bacon et al, Biochem. Biophys. Res. Comm., vol. 169 (3), pp. 1099–1104 (1990).
Bacon et al., Biochem. Biophys. Des. Comm., vol. 165 (1), pp. 349–354 (1989).
Dinarello et al., *New Engl. J. Med.* (1987) 317:940–945.
Schroder, *J. Exp. Med.* (1989) 847–863.
Schroder et al., *J. Immunol.* (1987) 139:3474–3483.

*Primary Examiner*—Jeffrey E. Russel
*Attorney, Agent, or Firm*—Kate H. Murashige

[57] ABSTRACT

A substance is prepared having interleukin-8 inhibiting activity by extracting psoriatic scales and separating the extract on several successive HPLC columns, using an assay for IL-8i activity based on the inhibition of myeloperoxidase release and/or of the neutrophil chemotaxis of a reference sample.

The substance is suitable for the preparation of anti-inflammatory medicines.

4 Claims, 5 Drawing Sheets

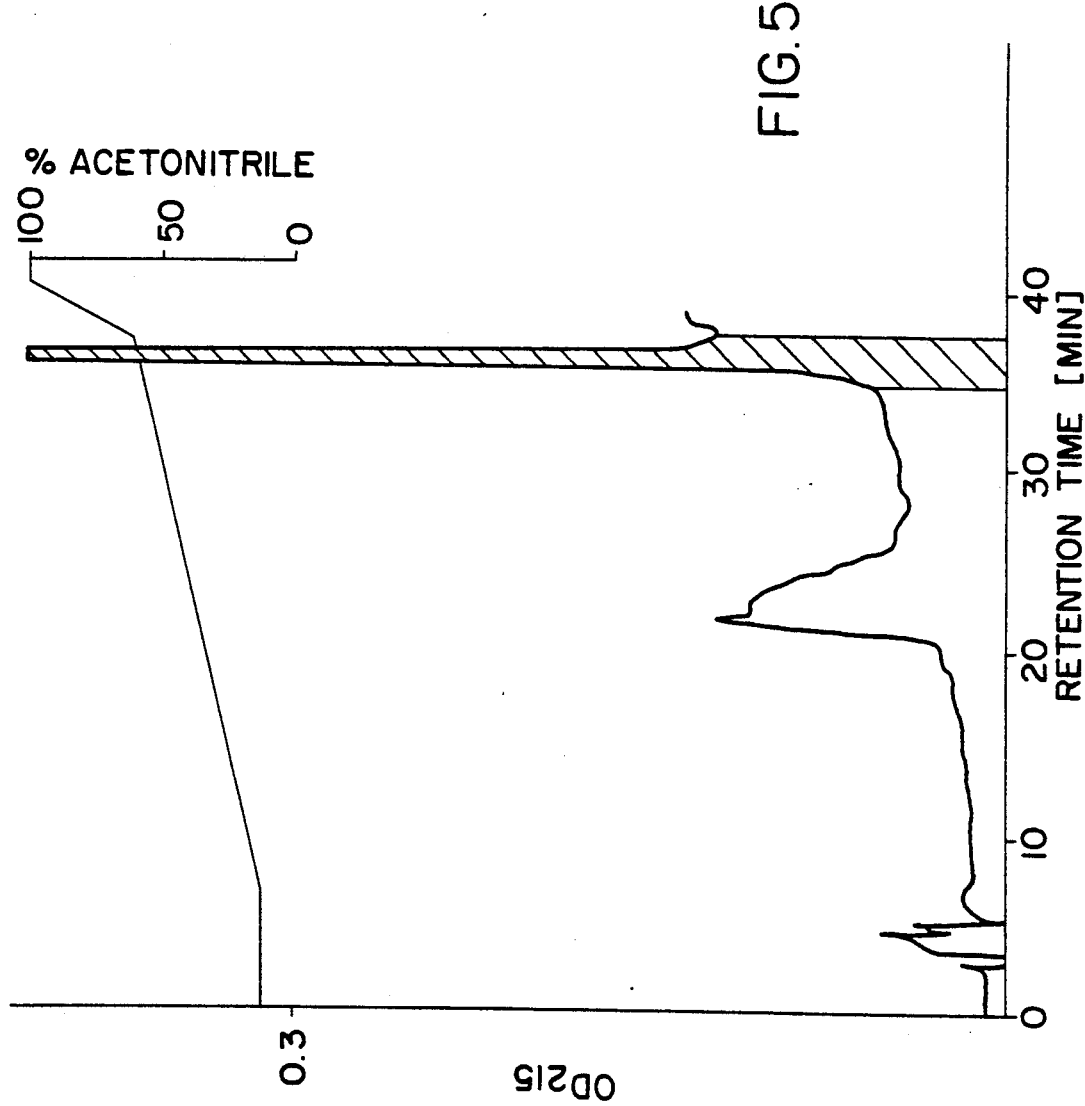

SUBSTANCE WITH INTERLEUKIN-8 INHIBITING ACTIVITY AND PROCESS FOR ITS PREPARATION

The present invention relates to a therapeutical substance which counteracts the effects of a cytokine and to a method for the preparation of that substance. Cytokines are soluble, multifunctional, peptide regulatory factors which occur in mammalian organisms and which play an important role in the regulation of cellular functions such as the mediation of inflammatory and immune reactions. They influence activation, proliferation and differentiation of both immune and non-immune cells. Cytokines are (glyco)proteins which bind to specific receptors. These hormone-like substances are released by lymphocytes, which explains the early name lymphokines, but also by other immune cells like macrophages or granulocytes and even by non-immune cells such as fibroblasts, endothelial cells, epithelial cells including keratinocytes and stroma cells. A more detailed description can be found e.g. in New England Journal of Medicine 1987, 317, 940-945.

One of the cytokines is interleukin-8 (IL-8), which has been shown to be a powerful substance for the initiation and the sustainment of inflammatory reactions. See e.g. international patent application WO 89/04325. IL-8 is also known under the names neutrophile activating peptide (NAP) or monocyte derived neutrophile activating peptide (MONAP). It attracts neutrophils by chemotaxis and triggers the release of myeloperoxidase. IL-8 is believed to be associated with diseases as psoriasis, allergic reactions, rheumatic afflictions and inflammations of the skin and the lung. The preparation and biochemical characterization of IL-8 are described in J. Exp. Med. 1989, 170, p.847 and in J. Immunol. 1987, 139, p.3474. The action of several cytokines is balanced by antagonists, but until presently no endogenous IL-8 antagonist has been found. In Strieter et al. (1989) and Van Damme et al. (1989) antibodies are described which are raised in animals against IL-8. There is a mention that these antibodies may inactivate IL-8 with regard to its chemotaxis.

The present invention provides IL-8 inhibitors, not being antibodies and denoted with the abbreviation IL-8i, which counteract the biological effects caused by interleukin-8. These inhibitory substances are obtainable from living organisms, particularly humans. A particularly suitable source of IL-8i has been found to be the scales of the involved skin of patients with psoriasis. When psoriatic scale extracts were analyzed by cationexchange-HPLC for proteins able to attract neutrophils (PMN) by chemotaxis, two broad peaks of activity could be isolated (FIG. 1). When fractions obtained from the same HPLC-run were tested for IL-8i-activity a broad area of fractions showed IL-8i-activity. Fractions having inhibitory activity (hatched area of FIG. 1) were pooled and further purified by, successively, preparative reversed-phase-HPLC (FIG. 2), cyanopropylHPLC (FIG. 3), TSK-2000-size-exclusion-HPLC (FIG. 4) and finally narrow pore RP-18-HPLC (FIG. 5). SDS-PAGE analysis of fractions of this RP-18-HPLC revealed two lines corresponding to proteins with a molecular weight of approximately 55 kDa and 70 kDa. The molecular weights are established by comparison with standard molecular weight markers. The IL-8 inhibitory substances are initially obtained as an aqueous solution of the active principles. When water and salts are removed from this solution, e.g. by lyophilization, a stable powder is obtained with IL-8 inhibitory activity. This powder may be purified further by preparative chromatography as described before.

The invention comprises also pharmaceutical preparations containing said substances or proteins. The IL-8i substances, either as a solution or as a powder, either in crude or in purified form, may be mixed with one or more usual pharmaceutically acceptable excipients, diluents and/or adjuvants to give a pharmaceutical preparation which is beneficial for the treatment of IL-8 mediated disorders such as psoriasis, allergic reactions, rheumatic afflictions and inflammatory diseases of the skin and the lung. In particular preparations are chosen which are suited for intravenous, subcutaneous, intralesional oral or topical administration. Often satisfactory results can be obtained with a pharmaceutical preparation of the crude isolate, but it is preferred to use the purified IL-8 inhibitor. The current medical treatment of inflammatory afflictions is not yet fully satisfactory. The medicines of preference are compositions containing steroids, particularly corticosteroids. But these medicines have several undesired side effects, especially when they are administered for a prolonged period. Known adverse symptoms are, for example, atrophy of the skin after topical application and inhibition of the adrenal cortex after systemic resorption. The pharmaceutical compositions according to the invention do not cause such side effects.

The IL-8i substances of the present invention can be isolated from an extract of psoriatic scales. The psoriatic scales are collected from the lesions of psoriatic patients. These scales are extracted with an ethanol/water mixture and a concentrate is made. Then the components are separated by chromatography using an eluens containing a gradient of ammonium formate.

It is also possible to obtain these substances by culturing host cells, particularly transformed microbial cells. This process comprises
  (a) Preparation of a DNA sequence capable of directing a host cell to produce a protein having IL-8 inhibitor activity,
  (b) Cloning the DNA sequence into a vector capable of being transferred into and replicated in a host cell, such vector containing operational elements needed to express the DNA sequence,
  (c) Transferring the vector containing the synthetic DNA sequence and operational elements into a host cell capable of expressing the DNA encoding the IL-8 inhibitor,
  (d) Culturing the host cells under conditions appropriate for amplification of the vector and expression of the inhibitor,
  (e) Harvesting the inhibitor and
  (f) Permitting the inhibitor protein to assume the active tertiary structure whereby it possesses IL-8 inhibitor activity. Host cells capable of expressing the IL-8i DNA are preferably chosen from the group comprising *E. coli, B. subtilis* and *K. lactis*.

BRIEF DESCRIPTION OF THE FIGURES

FIG. 5. The fractions in the hatched area of FIG. 4 were pooled and further separated in narrow pore reversed phase (RP-18) HPLC chromatography. Substance containing fractions (horizontal axis) eluted with a 1–100% acetonitril gradient are identified by peaks in the elution curve. Fractions which showed IL-8 inhibition according to the standard assay described later are marked by a hatched area.

EXAMPLES

Abbreviations

Figure 1:
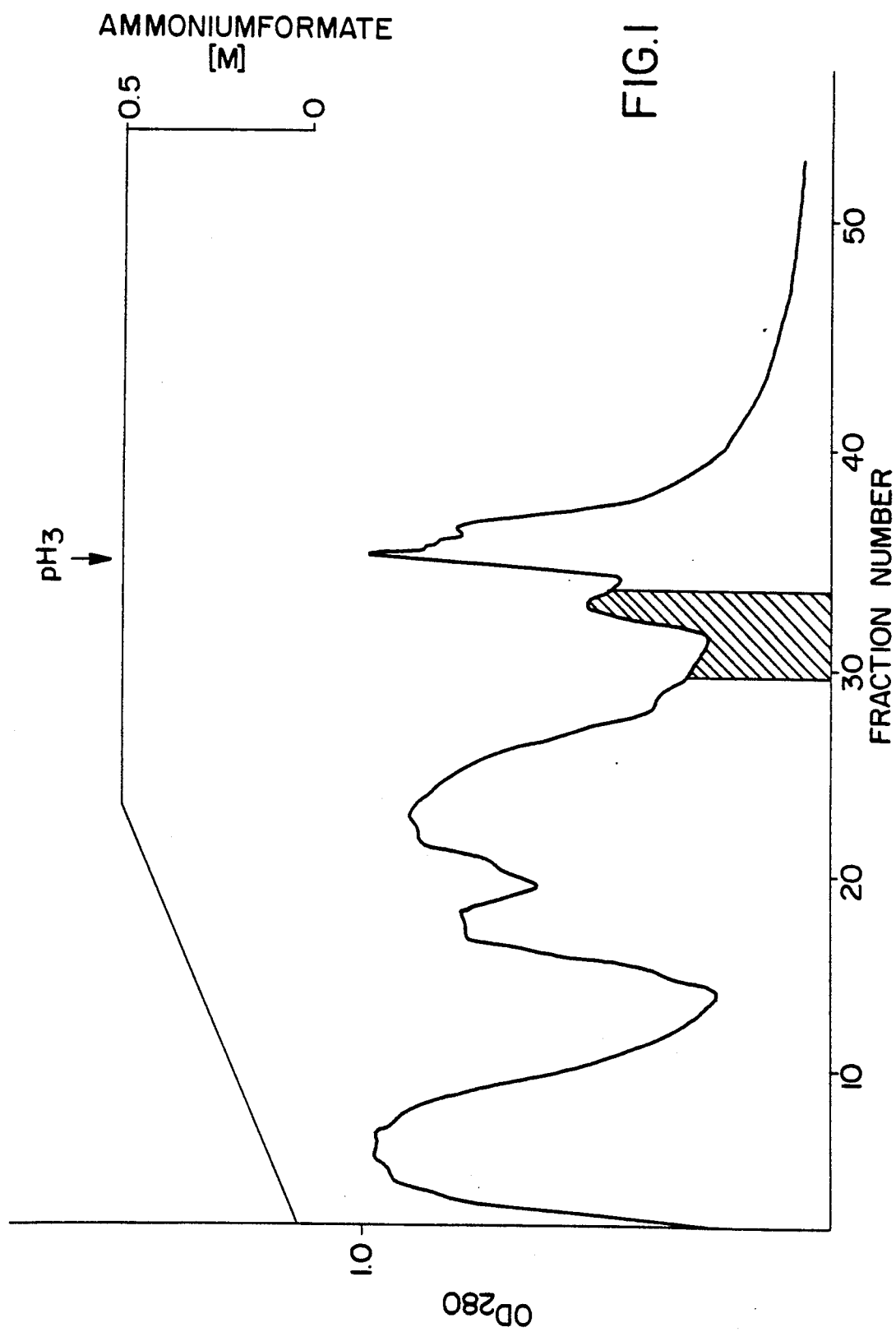
FIG. 1. A crude, diafiltered psoriatic scales extract was loaded on a cation exchange CM-TSK-HPLC column. Substance containing fractions (horizontal axis) eluted with a 0.01-0.5M formate gradient are identified by peaks in the elution curve. The IL-8 activity (MPO-release) of the same fractions is indicated by the lower bold line. The intermediate minimum in this curve points to the presence of IL-8i in the corresponding fractions, which fractions are marked by a hatched area. The upper line shows the concentration of the ammonium formate gradient.

| PMN | polymorphonuclear leukocytes, including neutrophils |
| --- | --- |
| PBS | phosphate buffered saline |
| BSA | bovine serum albumine |
| TFA | trifluoroacetic acid |
| MPO | myeloperoxidase |

Lit. ref. (1): J. Immunol. 1987, 139, p. 3474.

EXAMPLE 1

Preparation of polymorphonuclear leukocytes (PMN)

PMN are isolated from healthy donors blood, which is treated with EDTA as recently described in (1). PMN are separated from mononuclear cells by means of Hypaque/Ficoll gradients (1), followed by sedimentation with gelatine and ammoniumchloride lysis of erythrocytes (1). Cells are suspended in a buffered salt solution consisting of 138 mM NaCl, 2.7 mM KCl, 8.1 mM $Na_2HPO_4$, 1 mM $MgCl_2$, and 2.6 mM $CaCl_2$ (pH 7.4) (PBS) containing 0.1% (w/v) bovine serum albumine (type V, Sigma) to a final concentration of $2 \times 10^6$ PMN per ml containing 96±4% neutrophils.

EXAMPLE 2

Detection of substances inhibiting IL-8-related chemotaxis

According to an established method described in detail in J. Immunol. 1987, 139, p. 3474 the detection system of IL-8 related chemotaxis inhibiting substances uses the Boyden chamber technique with indirect counting of migrated PMN by the use of the "endogenous component chemotaxis assay" with $\beta$-glucuronidase as marker enzyme (1). Briefly, the lower part of the Boyden chamber is filled with 0.1 ml $10^{-9}$M IL-8 solution, prepared as described in J. Exp. Med. 1989, 170, p. 847, and dissolved in PBS containing 0.1% (w/v) bovine serum albumine, after which the lower part is covered with polycarbonat filters (3 μm pore size, Nuclepore) and thereafter the upper part is mounted. In the upper part 50 μl of a PMN suspension ($4 \times 10^6$ cells/ml) and 50 μl of appropriately prepared (lyophilized and dissolved with 100 μl PBS/BSA) IL-8i samples are mixed and incubated 1 h at 37° C. in a humidified atmosphere. Thereafter Boyden chambers are opened and migrated cells in the lower part are indirectly counted via their $\beta$-glucuronidase content as described in J. Immunol. 1987, 139, p.3474. The number of migrated cells is proportional to the concentration of active IL-8 in the lower part of the Boyden chamber. The difference with a reference line of a sample with a standard IL-8 concentration is a measure of the IL-8i activity present in the sample to be assessed.

EXAMPLE 3

Extraction of psoriatic scales

Scale material was collected from involved skin lesions of more than 100 patients with psoriasis. For biochemical analysis of PMN chemotactic polypeptides (IL-8) 50–100 g of psoriatic scale material was pooled, suspended in 800 ml 0.1M citric acid, adjusted to pH 3.0 with formic acid, homogenized using an Ultraturrax homogenizer for 1 to 2 hrs at 0° C. and then mixed with 30% (v/v) ethanol. After twofold freeze/thawing the mixture was centrifuged (2000×g, 30 min., 4° C.) and the supernatant, after concentrating to a small volume using an Amicon YMS filter (cut off: 5 kDa), stored below −70° C. until chromatographic separation.

EXAMPLE 4

Purification of IL-8-inhibiting protein (IL-8i)

A concentrated extract of psoriatic scales prepared according to example 3 was diafiltered against 0.01M ammonium formate, pH 5.0, and applied to a TSK-CM-SW-HPLC column (LKB, 12 mm×12 mm), which was previously equilibrated with 0.01M ammonium formate, pH 5.0. Proteins were eluted with a 0.01–0.5M gradient of ammonium formate, pH 5.0, and finally with 0.5M ammoniumformate acidified with formic acid to pH 3.0 (FIG. 1). 40–60 μl of each (2 ml) fraction were lyophylized over night in the presence of 10 μl 0.1% BSA in PBS to be tested subsequently for IL-8 (chemotaxis) inhibitory activity.

Figure 2:
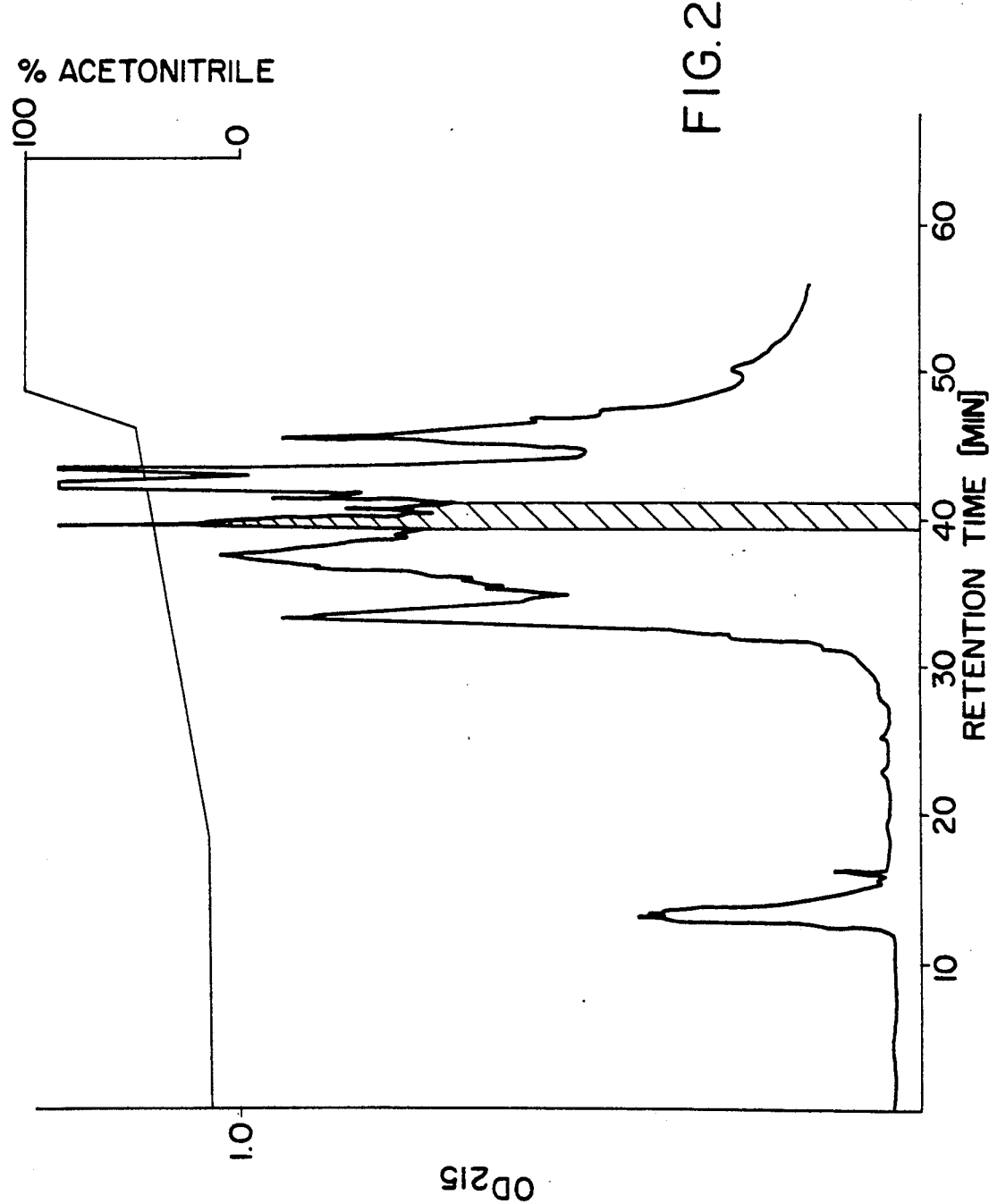
FIG. 2. The fractions in the hatched area of FIG. 1 were pooled and further separated in preparative wide pore reversed phase HPLC chromatography. Substance containing fractions (horizontal axis) eluted with an acetonitril gradient are identified by peaks in the elution curve. Fractions which showed IL-8 inhibition according to the standard assay described later are marked by a hatched area.

Fractions of the previous cation-exchange-HPLC containing IL-8i were further purified by preparative reversed phase (RP-8) HPLC chromatography. After acidification to pH 2.4 with trifluoroacetic acid (TFA) and diafiltration against 0.1% (v/v) TFA in water the IL-8i containing fractions were applied to a preparative wide pore reversed phase (C8) column (), 60×1.2 cm, Macherey and Nagel, which was previously equilibrated with water/acetonitrile/TFA (90:10:0.1, v/v/v). Polypeptides were eluted using a gradient of increasing concentrations of acetonitrile containing 0.1% TFA with a flow rate of 2 ml/min (FIG. 2). 40 µl of each fraction were lyophilized and tested for IL-8i activity.

Figure 3:
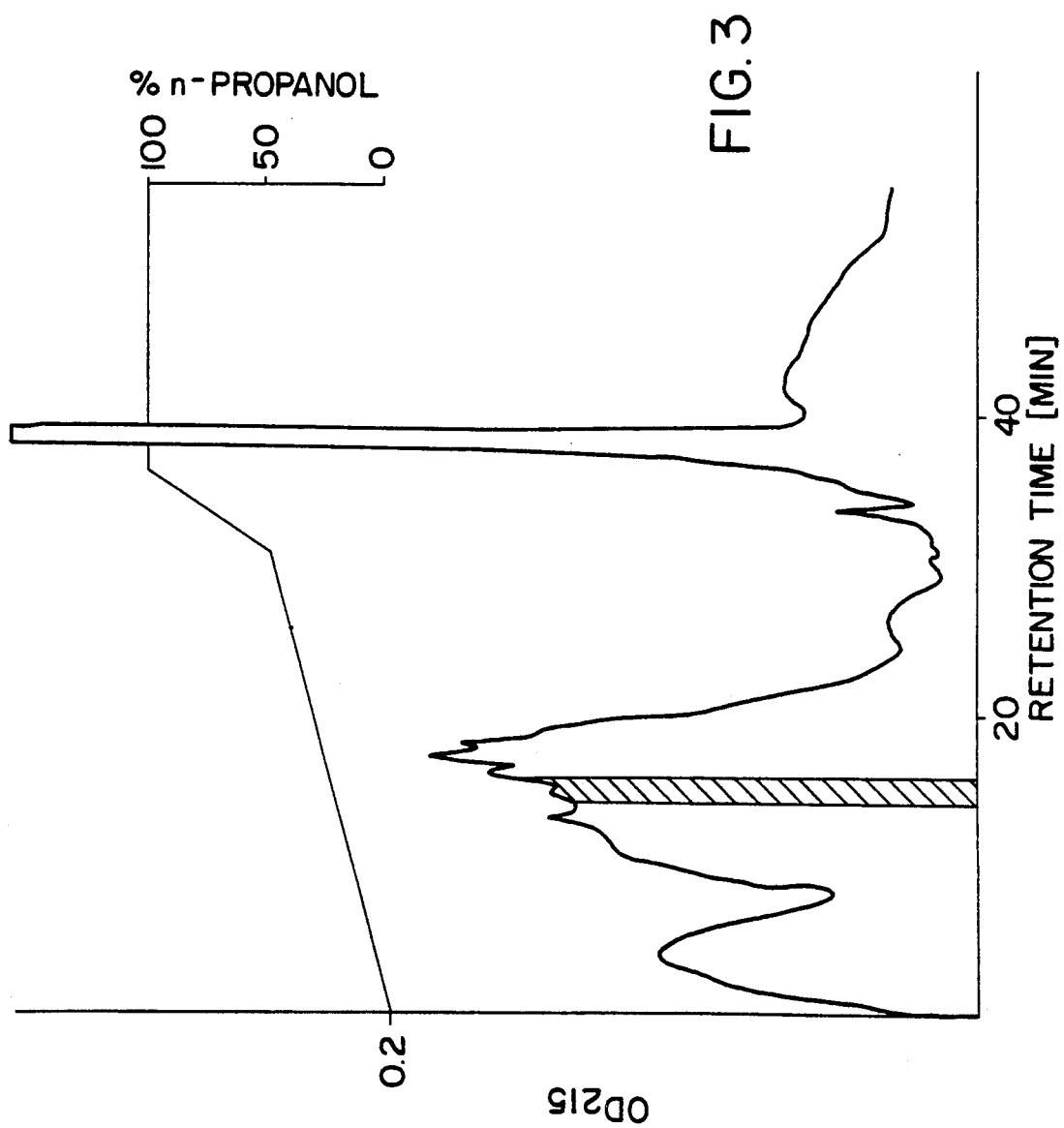
FIG. 3. The fractions in the hatched area of FIG. 2 were pooled and further separated in analytical wide pore cyanopropyl HPLC chromatography. Substance containing fractions (horizontal axis) eluted with a 0–100% n-propanol gradient are identified by peaks in the elution curve. Fractions which showed IL-8 inhibition according to the standard assay described later are marked by a hatched area.

Further purification of fractions having IL-8i activity was performed using cyanopropyl HPLC. Fractions of reversed phase (RP-8) HPLC were lyophylized and the residue dissolved in 0.1% TFA in water and applied to an analytical wide pore cyanopropyl HPLC column (5 µm, 250 ×4.6 mm, J. T. Baker, Gross Gerau, FRG) previously equilibrated with the same solvent. Proteins were eluted using a 0-100% n-propanol gradient containing 0.1% TFA (FIG. 3). IL-8i activity was estimated subsequently.

Figure 4:
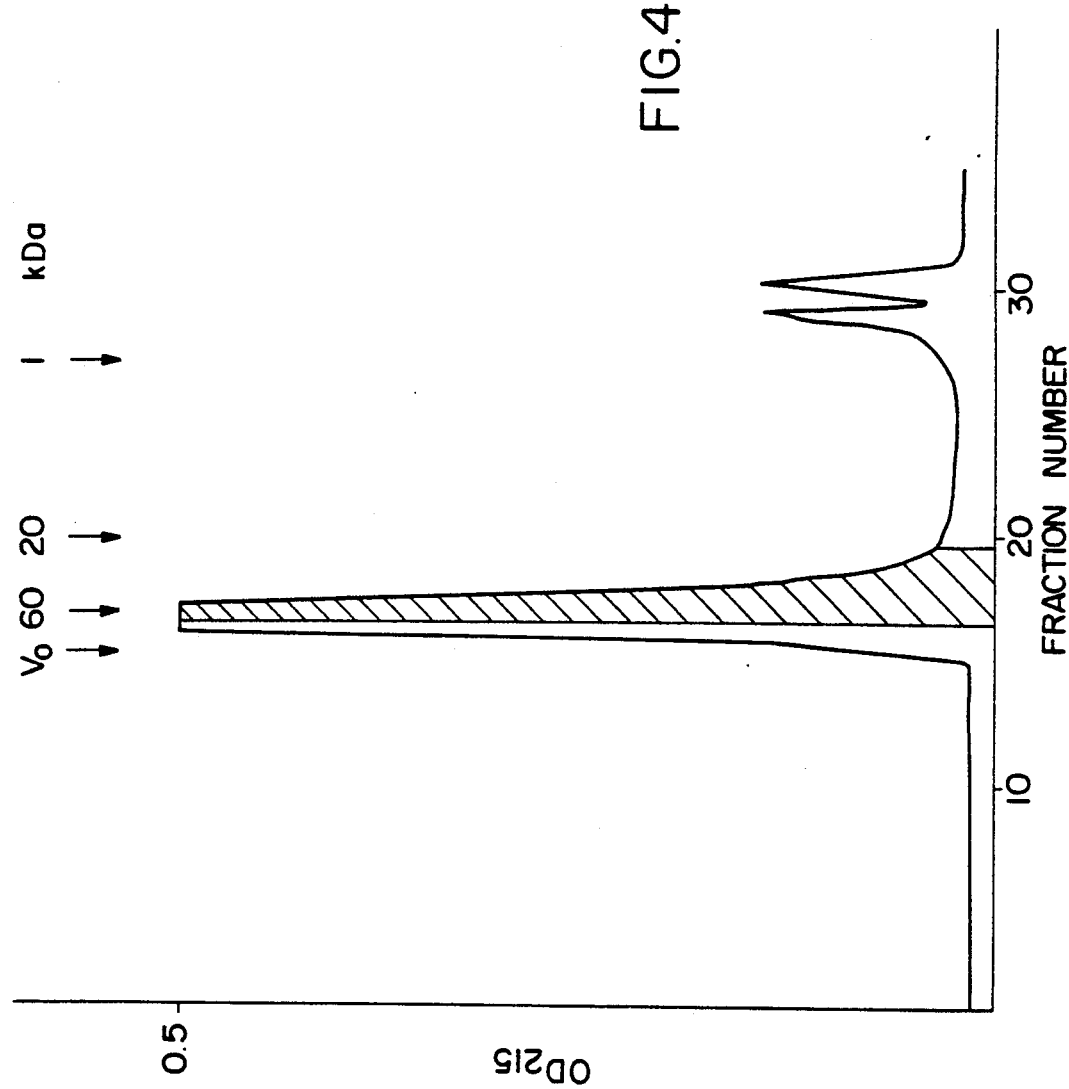
FIG. 4. The fractions in the hatched area of FIG. 3 were pooled and further separated in TSK-2000-3SW size exclusion HPLC chromatography. Substance containing fractions (horizontal axis) eluted with a 0.1% TFA in water solution are identified by peaks in the elution curve. Fractions which showed IL-8 inhibition according to the standard assay described later are marked by a hatched area.

IL-8i containing fractions of the previous purification step were lyophylized and the residue dissolved in 200 µl aqueous TFA (0.1%) and applied to a TSK-2000-3SW size exclusion-HPLC-column (1.4×60 cm containing a 1.4×20 cm precolumn, Pharmacia, Uppsala, Sweden) previously equilibrated with 0.1% TFA in water. Proteins were eluted with the same eluent at a flow rate of 1 ml/min (FIG. 4).

IL-8i containing fractions of the previous chromatographic separation were finally purified by narrow pore reversed phase (RP-18) HPLC using a 1-100% acetonitril gradient for elution. Fractions containing IL-8i were analyzed by SDS-PAGE using a Phast-system (Pharmacia) and a homogeneous 20% gel. After visualization with silver staining (Sigma) the presence was proved of proteins with molecular weights of approximately 55 kDa and 70 kDa.

We claim:

1. A protein obtainable from humans and provided in purified and isolated form, which has interleukin-8 inhibiting activity (IL-8i); and is selected from the group of proteins having a molecular weight of approximately 55 kDa and 70 kDa as assessed in a gel filtration size exclusion column and is other than an antibody against IL-8.

2. The composition of claim 1 which is obtainable by a process which comprises:
   (a) mixing psoriatic scales with a 0.1M citric acid solution,
   (b) adjusting to pH 3 with formic acid,
   (c) homogenizing until a suspension is obtained,
   (d) mixing with 30% (v/v) ethanol,
   (e) freeze/thawing and concentrating the mixture,
   (f) diafiltering the concentrate against ammonium formate,
   (g) separating the dissolved matter in chromatographic fractions,
   (h) testing fractions for IL-8 inhibitory activity, and
   (i) selecting positive fractions.

3. A pharmaceutical composition comprising a pharmaceutically effective amount of at least one protein of claim 1 in admixture with a pharmaceutically acceptable excipient.

4. The protein of claim 1 which has a molecular weight of approximately 55 kDa.

* * * * *